(12) United States Patent
Ovod

(10) Patent No.: US 8,878,920 B2
(45) Date of Patent: Nov. 4, 2014

(54) METHOD AND APPARATUS FOR PROTECTION FROM HIGH INTENSITY LIGHT

(75) Inventor: Vladimir I. Ovod, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 429 days.

(21) Appl. No.: 13/181,350

(22) Filed: Jul. 12, 2011

(65) Prior Publication Data
US 2013/0016200 A1   Jan. 17, 2013

(51) Int. Cl.
| | | |
|---|---|---|
| H04N 7/18 | (2006.01) | |
| H04N 5/235 | (2006.01) | |
| A61B 1/06 | (2006.01) | |
| A61B 1/04 | (2006.01) | |
| G03B 15/03 | (2006.01) | |
| A61B 1/00 | (2006.01) | |
| G03B 15/14 | (2006.01) | |

(52) U.S. Cl.
CPC .............. *H04N 5/2354* (2013.01); *H04N 7/18* (2013.01); *A61B 1/06* (2013.01); *G03B 15/03* (2013.01); *H04N 5/2352* (2013.01); *A61B 1/00006* (2013.01); *A61B 1/00009* (2013.01); *A61B 1/042* (2013.01); *A61B 1/0669* (2013.01); *G03B 15/14* (2013.01)
USPC ........................................... 348/68; 356/317

(58) Field of Classification Search
CPC ............ H04N 7/18; G01J 3/427; G01J 3/443; G02B 26/08
USPC ................... 348/68, E07.085; 356/317, 320; 600/160, 473, 476, 118, 176; 702/64; 345/84
See application file for complete search history.

(56) References Cited

U.S. PATENT DOCUMENTS

| | | |
|---|---|---|
| 3,670,722 A | 6/1972 | Kosaka |
| 4,356,534 A | 10/1982 | Hattori |
| 4,366,529 A | 12/1982 | Takahashi et al. |
| 4,415,952 A | 11/1983 | Hattori et al. |
| 4,433,675 A | 2/1984 | Konoshima |
| 4,509,508 A | 4/1985 | Tsukaya |
| 4,527,552 A | 7/1985 | Hattori |

(Continued)

FOREIGN PATENT DOCUMENTS

JP       62155689 A       7/1987

OTHER PUBLICATIONS

"A Robust Multistage Algorithm for Camera Self-Calibration Dealing With Varying Intrinsic Parameters" Adnane El-Attar, Mohammed Karim, Hamid Tairi, Silviu Ionita, E-ISSN: 1817-31.*

(Continued)

*Primary Examiner* — Dave Czekaj
*Assistant Examiner* — Dramos I Kalapodas
(74) *Attorney, Agent, or Firm* — St. Onge Steward Johnston & Reens LLC

(57) ABSTRACT

A method and apparatus where the output from a high intensity light source is controlled to produce well-exposed images/videos and to reduce automatically the intensity when an unsafe issue is detected in medical devices such as endoscopes and the like. The method and apparatus overcome problems to control light sources that have high-frequency noise, slow-response time, nonlinearity, and non-monotonic response time and to protect the patients' tissues from possible overheating/burning and the eyes of personnel and patients from possible direct exposure to high intensity light used in medical devices such as endoscopes and the like.

39 Claims, 8 Drawing Sheets

(56) References Cited

U.S. PATENT DOCUMENTS

| | | | |
|---|---|---|---|
| 4,561,429 A | 12/1985 | Sato et al. | |
| 4,963,960 A | 10/1990 | Takami | |
| 5,091,779 A | 2/1992 | Ams et al. | |
| 5,131,381 A | 7/1992 | Ams et al. | |
| 5,134,469 A | 7/1992 | Uchimura | |
| 5,159,380 A | 10/1992 | Furuya et al. | |
| 5,162,913 A | 11/1992 | Chatenever et al. | |
| 5,475,420 A * | 12/1995 | Buchin | 348/72 |
| 5,749,830 A * | 5/1998 | Kaneko et al. | 600/160 |
| 5,957,934 A | 9/1999 | Rapoport | |
| 6,464,633 B1 * | 10/2002 | Hosoda et al. | 600/178 |
| 6,511,422 B1 | 1/2003 | Chatenever | |
| 6,707,485 B1 | 3/2004 | Higuchi et al. | |
| 6,734,894 B1 | 5/2004 | Higuchi et al. | |
| 6,767,320 B2 | 7/2004 | Farkas et al. | |
| 6,856,436 B2 * | 2/2005 | Brukilacchio et al. | 359/204.2 |
| 7,070,560 B2 | 7/2006 | Takahashi | |
| 7,077,804 B2 | 7/2006 | Ota | |
| 7,140,893 B2 | 11/2006 | Abe et al. | |
| 7,235,045 B2 * | 6/2007 | Wang et al. | 600/109 |
| 7,247,135 B2 | 7/2007 | Iriyama | |
| 7,336,894 B2 | 2/2008 | Ito | |
| 7,556,414 B2 | 7/2009 | Hopkins et al. | |
| 7,563,010 B2 | 7/2009 | Bimkrant et al. | |
| 7,585,276 B2 | 9/2009 | Itoi | |
| 7,798,959 B2 | 9/2010 | Negishi | |
| 7,828,726 B2 | 11/2010 | Negishi | |
| 7,847,817 B2 | 12/2010 | Negishi | |
| 7,853,106 B2 | 12/2010 | Takahashi et al. | |
| 8,403,835 B2 * | 3/2013 | Matsuura | 600/177 |
| 2004/0186382 A1 * | 9/2004 | Modell et al. | 600/473 |
| 2005/0020926 A1 * | 1/2005 | Wiklof et al. | 600/476 |
| 2007/0156021 A1 * | 7/2007 | Morse et al. | 600/167 |
| 2007/0183162 A1 * | 8/2007 | Higuchi | 362/458 |
| 2008/0287742 A1 * | 11/2008 | St. George et al. | 600/160 |
| 2010/0067002 A1 * | 3/2010 | Ishii | 356/317 |
| 2011/0246109 A1 * | 10/2011 | Fafard | 702/64 |

OTHER PUBLICATIONS

Journal of Theoretical and Applied Information Technology; E-ISSN:1817-31.*

Journal of Theoretical and Applied Information Technology; vol. 31 No. 1, Oct. 15, 2011;E-ISSN:1817-31.*

European Search Report Application No. EP 12 17 6218 Completed: Oct. 19, 2012 Mailing Date: Nov. 6, 2012 10 pages.

Anonymous: "Exposure (photography)" Wikipedia, the free encyclopedia; XP002685566; Retrieved From the Internet: URL:http//en.wikipedia.org/wiki/Exposure_%28photography%29 Retrieved on Oct. 18, 2012.

Anonymous: "Exposure Value" Wikipedia, the free encyclopedia; XP002685565; Retrieved From the Internet: URL: http//en.wikipedia.org/wiki/Exposure_value Retrieved on Oct. 18, 2012.

Anonymous: "Flash (photography)" Wikipedia, the free encyclopedia; XP002685567; Retrieved From the Internet: URL:http//en.wikipedia.org/wiki/Flash_%28photography%29 Retrieved on Oct. 18, 2012.

Anonymous: "Light Meter" Wikipedia, the free encyclopedia; XP002685568; Retrieved From the Internet: URL:http//en.wikipedia.org/wiki/Exposure_meter Retrieved on Oct. 18, 2012.

* cited by examiner

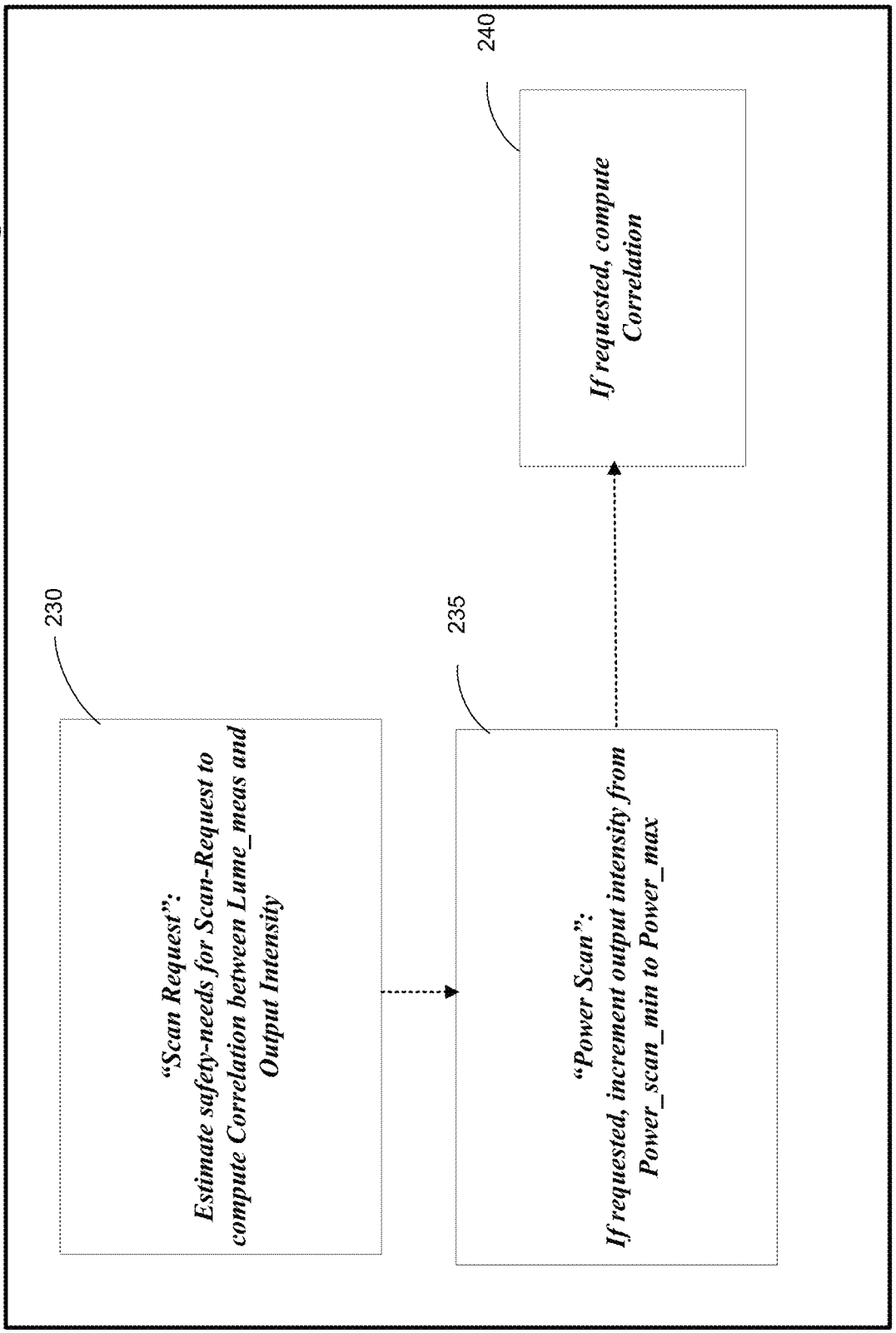

METHOD AND APPARATUS FOR PROTECTION FROM HIGH INTENSITY LIGHT

FIELD OF THE INVENTION

This invention generally relates to a method and apparatus for automatically protecting personnel and patients from direct exposure to the output of a high intensity light source used in medical devices, such as endoscopic imaging systems and the like. The invention also generally relates to a method and apparatus for overcoming problems to control high intensity light sources that have high-frequency noise, slow-response time, nonlinearity, and non-monotonic response time, such as Xenon or Xenon-like based light sources.

BACKGROUND OF THE INVENTION

The imaging of body surfaces through an endoscope is well known within the medical and veterinarian fields. Typically, this involves inserting an endoscope into a body cavity and directing a high intensity light source output through the endoscope to illuminate body tissue. Light reflected by the body tissue then is guided along an optical path to an image sensor to generate both video and still images of the tissue. One such approach is described in U.S. Pat. No. 5,162,913 to Chatenever et al., and provides a technique for an automatic adjustment of the exposure of video images detected with a CCD (charge coupled device) image sensor.

The use of high intensity light sources involves potential hazards to medical personnel and patients. For example, when a light guide cable, used to convey the high intensity-light source output, is momentarily disconnected from the endoscope and placed on a sterile drape used to protect the patient, the high intensity of light output can be sufficient to ignite the drape and pose a fire hazard; or, the user can inadvertently hold the disconnected light guide cable in such a way as to temporarily blind another person in the room. In some instances, when the endoscope is removed from (i.e., pulled out of) a patient, there can be a risk of these same hazards. When the light source is used with an endoscopic video camera, which has an automatic exposure system, the light source output intensity may be turned up to a intensity level higher than required for the camera to produce well-exposed images. This increased light intensity level can desiccate body tissue and cause serious injury to the patient. Typically, endoscopic video camera automatic exposure systems can produce well-exposed images with an electronic shutter setting of approximately $\frac{1}{125}^{th}$ to $\frac{1}{500}^{th}$ of a second. If the distal end of an endoscope is placed within close proximity to tissue being imaged, typically, a relatively lower light intensity level will still enable an endoscopic video camera to produce well-exposed images. An undesirable, and potentially dangerous, scenario can occur if the light source output is set to a high intensity level, and the endoscope distal end is placed within close proximity to tissue being imaged. Typically, in such a case, automatic camera exposure systems will adjust the electronic shutter setting to approximately $\frac{1}{10,000}^{th}$ of a second (or faster) to compensate for the high illumination reflections from the tissue. In such a situation, the risk of desiccating delicate tissue is greatly increased.

Thus, it is desirable to solve these problems, specifically to control the output from a high intensity light source so that the light source intensity is automatically reduced to a safe level when the light source output is not directed to a surface and/or the camera/imager or light-guide are disconnected from each other. It is also desirable to protect tissues operated on during a surgical procedure from overheating or burning due to the intensity of the light source being set higher than required to produce well-exposed images. It is also desirable to protect the eyes of the operator of an endoscope or persons in the surgical area from direct exposure to high intensity light used in medical devices such as endoscopes and the like.

Techniques for controlling the output intensity from a light source are known in the art. For example, a technique for automatically controlling the light intensity from a light source, on the basis of an image signal from an imaging unit associated with an endoscope, is described in Japanese Unexamined Patent Publication No. 62-155689 as mentioned at column 2, lines 1-21 in U.S. Pat. No. 5,957,834 to A. Mochida. As recognized in the Mochida patent, when light intensity control is made dependent upon a signal derived from the image, then upon removal of the endoscope from the body, the control is likely to increase the output intensity level from the light source, when instead it should decrease the output to protect the operator's eyes from inadvertent high intensity light exposure and prevent ignition of combustible material. In the Mochida patent, a switch is added to manually adjust and control the output of the light source when the endoscope is removed from a body.

As further described in the Mochida patent, the output intensity level of the light source is controlled by regulating the position of a diaphragm with respect to the light source. The control signal for doing this is derived from an image sensor in the endoscope.

In U.S. Pat. No. 4,527,552 a photoelectric element generates a signal indicative of the intensity of light reflected from an object illuminated by a light source associated with the endoscope to control the light source output level. In U.S. Pat. No. 5,131,381 a light source associated with an endoscope is controlled by a signal that represents the density value of each line of a camera video image derived through the endoscope. Other patents relevant to light intensity level controls for endoscopes are U.S. Pat. Nos. 3,670,722; 4,963,960; 4,561,429; 5,091,779; 5,134,469; 5,159,380; 6,767,320; 7,070,560; 7,585,276; 7,798,959; 7,847,817; and 7,828,726.

Techniques have been proposed to reduce the risks associated with high intensity light sources. One involves a special light guide cable with wires in it that are shorted together when the cable is attached to an endoscope. The short is detected at the light source and light output intensity is reduced when the cable is disconnected and the short is subsequently removed. A retractable mechanical shroud, which covers the light guide cable end when not connected to an endoscope, has also been suggested.

These safety solutions are not necessarily effective against all potential hazardous conditions that may arise; such as when the endoscope with the light guide cable still attached is pulled out of a patient and inadvertently directed at a person or surgical drape, or when the light guide or source initially is directed to treat openly accessible tissue and inadvertently misdirected during or after a procedure, or when a video camera head, attached to the endoscope light guide cable combination, is disconnected from its corresponding control unit.

One such approach to solve this problem is described in U.S. Pat. No. 6,511,422 to Chatenever (hereinafter Chatenever '422). Chatenever '422, herein incorporated by reference, describes a method and apparatus where the output from a high intensity light source is controlled so that whenever the output is not directed at tissue (meaning that the endoscope/video camera/light source combination is not currently being used to image body tissue), the light source output intensity is automatically reduced to a safer level. This is done by monitoring the reflected light from tissue and when this reflection indicates that the light source is not directed at tissue, the light intensity is turned down to a safer level. This involves generating a modulation signal and modulating the intensity of the light source output with the modulation signal.

Chatenever '422 involves monitoring the light reflected by a surface, detecting the modulation in the monitored light, and reducing the intensity of the light source output when the detected modulation is below a reference level. However, Chatenever '422, while effective as a safety solution, has problems controlling Xenon lights and other light sources because the amplitude or frequency modulation methods described by Chatenever '422 do not work well with light sources having these problems. Specifically, Chatenever '422 does not work well with lights sources that have slow-response, high-frequency noise, nonlinearity, and non-monotonic response times, such as Xenon lights. It is thus desirable to provide an improved method and apparatus that works with light sources that have slow-response, high-frequency noise, nonlinearity, and non-monotonic response times.

It is also desirable to improve upon the methods and apparatus described in the Chatenever '422 patent to overcome problems to control Xenon light sources, as Xenon light sources have increased applicability in endoscope technology. None of the other existing methods and apparatuses described in the prior art work effectively with light sources that have slow-response, high-frequency noise, nonlinearity, and non-monotonic response times.

It is further desirable to provide a method and apparatus to upgrade existing and future endoscopic imaging systems with a light source control ("LSC") feature that solves problems associated with light sources, such as Xenon lights. It is also desirable to do so in a cost effective way, and without any hardware change in product lines of light sources and endoscopic imaging systems.

It is also desirable to design a cost-effective single LSC implementation based on the method that is suitable for various existing and yet to be developed product lines of light sources, camera heads, camera control units ("CCUs"), videoscopes, and endoscopes. It is also desirable to provide software that executes upon hardware.

It is also desirable to provide a method and apparatus for LSC that enables adaptive normalization and self-calibration; so as to simplify the adjustment of the LSC feature to new endoscopic imaging systems and light sources and to minimize manual adjustment.

It is also desirable to provide a self-recovery method that involves the adaptive normalization and self-calibration techniques, so as to recover and/or optimize the LSC feature to possible new vs. replacement of light source and/or the type of the scope attached to the camera during surgery, and/or the camera type of CCU during use and/or surgery.

SUMMARY OF THE INVENTION

Accordingly, it is an object of the present invention to provide a method and apparatus to overcome known problems when working to control light sources that have slow-response, high-frequency noise, nonlinearity, and non-monotonic response times.

It is an object of the invention to provide a method for upgrading existing and newly-designed endoscopic imaging systems with a light source control ("LSC") feature that controls the intensity of the light source output. It is an object of the invention to reduce and/or eliminate costs associated with upgrading of existing and newly-designed endoscopic imaging systems with the LSC feature without any hardware change in product lines of light sources, camera-heads/imagers, CCUs, videoscopes, and endoscopes.

It is an object of the invention to provide a cost-effective single LSC implementation that is suitable for existing and newly-developed or in-development product lines of light sources, camera-heads/imagers, CCUs, videoscopes, and endoscopes.

It is an object of the invention to provide a method and apparatus that enables adaptive normalization and self-calibration, so as to simplify the adjustment of the light control feature to new camera heads/imagers, CCUs, endoscopes, videoscopes, and light sources.

It is an object of the invention to provide a self-recovery method that involves adaptive normalization and self-calibration, so as to recover and/or optimize the LSC feature by adding new or replacement components to the LSC system. Adding such new or replacement components can be added during use and/or surgery.

It is an object of the present invention to control the output from a high intensity light source so that the output intensity is automatically set at a reasonable and safe level while producing well-exposed images.

It is an object of the present invention to protect personnel and patients from direct exposure to high intensity light used in medical devices such as endoscopes and videoscopes by automatically reducing the light source output intensity to a safe level when a safety-failure is detected. It is an object of the invention to provide a failure-detection method that detects when the light source output is not directed to a surface, when the camera/imager and/or light-guide are disconnected, and when no motion is detected in the video image.

It is an object of the present invention to protect tissues from overheating/burning when the distal end of an endoscope is placed within close proximity to tissue by automatically reducing the light source output to a safe level while still producing well-exposed images.

These and other objects of the invention are achieved by providing an apparatus for viewing a surface comprising: an examining instrument, the examining instrument having an imaging path through which the surface is observed; a light source, the light source illuminating the surface; an imager, the imager detecting light reflected from the surface, and generating image signals; a camera control unit (CCU), the CCU processing the image signals; and a controller associated with the imager and CCU, the controller decrementing or incrementing the intensity of the light source output via at least two steps.

The controller of the apparatus may decrement or increment the intensity of the light source output via a plurality of steps. The intensity of the at least two steps and/or plurality of steps may be incremented or decremented in intervals as small as 1% of the total light source intensity output. The power intervals incremented or decremented may be in steps that are greater than 1% (i.e. 3%, 5%, 15%) or in steps less than 1% (i.e. 0.25%, 0.5%) of the total light source output intensity; depending upon the operational characteristics of the light source, camera head/imager, CCU, and other devices being utilized. The magnitude of the at least two steps may be incremented or decremented by a predetermined percentage of the maximum light source output intensity.

The apparatus may further comprise a communication bus coupled to a plurality of bus interfaces for communication between the light source, CCU, and camera.

The light source of the apparatus may be a Xenon or Xenon-like based light source. The light source may have at least one of a high-frequency noise, slow-response time, non-linearity, and non-monotonic response time.

The examining instrument of the apparatus may be selected from a group consisting of an endoscope, laryngoscope, bronchoscope, fiberscope, duodenoscope, gastroscope, flexible endoscope, arthroscope, cystoscope, laparoscope, anoscope, and sigmoidoscope.

The controller of the apparatus may process the image signals representative of light reflected from the tissue/scene as detected by the imager.

The imager (or image sensor) may be located distally inside the examining instrument, proximally inside the examining instrument, or externally from the examining instrument. The imager may be a CCD, CMOS, or imager types yet to be developed.

The apparatus may further comprise software executing on the controller. The software involves operating the controller such that the software allows for the apparatus to operate. The software may involve various specific parameters that allow for the apparatus and controller to operate.

In one example, the software may operate by including an exposure value $EV_i$ (i.e., the shutter speed in seconds), $EV_i$ being used to control the output intensity of the light source. The measured $EV_i$ is referred to as $EV_{meas}$, and when $EV_{meas}$ is below a threshold $EV_{tr}$, the light source output intensity is reduced. $EV_i$ is referred to as the shutter speed. It may be determined in seconds or other such units of time for measuring the shutter speed.

The optimal value of $EV_i$ is referred to as $EV_{opt}$, and is between $EV_{opt,min}$ and $EV_{opt,max}$, wherein $EV_{opt}$ depends on $EV_{meas}$, the monotonic and linearity characteristics of the light source output.

If $EV_{meas}$ is less than $EV_{opt,min}$, the output intensity of the light source is incremented, if $EV_{meas}$ is greater than $EV_{opt,max}$, the output intensity of the light source is decremented, and if $EV_{meas}$ is between $EV_{opt,min}$ and $EV_{opt,max}$, the output intensity of the light source is unchanged.

The criteria to form a well-exposed image requires that $EV_{meas}$ be between $EV_{opt,min}$ and $EV_{opt,max}$. The software executing on the controller operates such that $EV_{meas}$ is between $EV_{opt,min}$ and $EV_{opt,max}$ so that well-exposed images are taken.

The apparatus of various embodiments of the invention minimizes the number of increments or decrements of light output intensity. It is advantageous to minimize the number of increments or decrements of light output intensity and to do so in a stepwise manner.

The controller of the apparatus may include a scan request method for detecting a potential safety issue when the light source output intensity ("P") is potentially unsafe. Once a potential safety issue is detected via the scan request method, the apparatus may enable the power scan and the correlation methods, and disable the EV method. The power scan method being able to increment or decrement the output intensity of the light source with a specified step $\Delta P_{scan}$, from $P_{scan,min}$ to $P_{max}$, and vice-versa, where $P_{scan,min}$ is less than $P_{max}$, and $P_{max}$ is the maximum allowed light source output intensity. The output intensity may be incremented via steps from $P_{scan,min}$ to $P_{max}$. Optionally, the output intensity may be decremented via steps from $P_{max}$ to $P_{scan,min}$.

The power scan method may be enabled by a scan request method, the scan request method being able to detect a potential safety issue.

Furthermore, the controller may compensate for the prior-art shortcomings and disadvantages of detecting a modulation within the output of a Xenon or a Xenon-like based light source, due to high frequency noise, slow, nonlinear, and non-monotonic response, by using the scan request method that includes a correlation method allowing for detecting when the light source output is not directed at a surface, and for decrementing the output intensity with a specified step $\Delta P_{scan}$ until a safe output level is reached. When the scan request method detects a potential safety issue, the correlation method is enabled and the EV method is disabled, and wherein when a potential safety issue is not detected, the correlation method is disabled and the EV method is enabled.

The apparatus may involve having the output intensity of the light source be automatically reduced to a safe level when the light source output is not directed to a surface. The intensity of the light source may be automatically reduced to a safe level when at least one of the camera head, image sensor and light source and/or light guide are disconnected.

The controller may include adaptive normalization and self-calibration. The adaptive normalization may include normalizing EV and recomputing calibration curves based on the type of light source and image sensor. The adaptive normalization and self-calibration may depend upon image sensor integration time $T_{int}$, and also the value of $EV_{min}$ and $EV_{max}$.

The controller may also include a self-recovery method that involves adaptive normalization and self-calibration, so as to recover and/or optimize the LSC feature. This involves adaptive normalization and self-calibration when components in the system are changed or replaced during use and/or surgery. Components that are replaced and/or changed are the type of scope attached to the camera, the light source, the camera, any videoscopes, endoscopes and/or CCU devices. Other components in the system may also be replaced.

The self-recovery method may protect from possible failure of the LSC caused by the new and/or replacement components during surgery.

The controller may detect when no motion or the lack of motion is detected in the video images so as to decrease output intensity to a safe level. The controller may compensate the slow response of a Xenon or a Xenon-like light source by inserting optimal delays before and/or after controlling of light source. In certain embodiments, the controller may not be continuously enabled in order to minimize flickering of the images.

Other objects of the invention are achieved by providing an apparatus for viewing a surface comprising: an examining instrument, the examining instrument having an imaging path through which the surface is observed; a light source, the light source illuminating the surface; an imager, the imager detecting light reflected from the surface, and generating image signals; a camera control unit (CCU), the CCU processing the image signals; and a controller associated with the imager and CCU, the controller decrementing the intensity of the light source output via at least two steps. The controller may also have light source output intensity incrementing ability in certain embodiments.

The examining instrument may be selected from a group consisting of an endoscope, laryngoscope, bronchoscope, fiberscope, duodenoscope, gastroscope, flexible endoscope, arthroscope, cystoscope, laparoscope, anoscope, and sigmoidoscope.

Other objects of the invention are achieved by providing a method for controlling the light output intensity of a light source comprising: measuring an exposure value $EV_i$, $EV_i$ being used to control the output intensity of the light source; and incrementing or decrementing the output intensity of the light source based upon the exposure value $EV_i$.

The method may have software executing, the software being able to execute upon hardware.

The method may have a measured $EV_i$ be $EV_{meas}$, and when $EV_{meas}$ is below the threshold $EV_{tr}$, the light source output intensity is immediately set to a safe level.

The method may have the optimal value of $EV_i$ be $EV_{opt}$, which is between $EV_{opt,min}$ and $EV_{opt,max}$, wherein $EV_{opt}$ depends on $EV_{meas}$, and the monotonic and linearity characteristics of the light source.

If $EV_i$ is less than $EV_{opt,min}$, the output intensity of the light source is incremented, if $EV_i$ is greater than $EV_{opt,max}$, the output intensity of the light source is decremented, and if $EV_i$ is between $EV_{opt,min}$ and $EV_{opt,max}$, the output intensity of the light source is unchanged. The criteria to form a well-exposed image requires that $EV_{meas}$ be between $EV_{opt,min}$ and $EV_{opt,max}$.

The method may further comprise the step of incrementing the output intensity of the light source via a power scanning step, the power scanning step allowing for incrementing the output intensity of the light source a few times with a specified step $\Delta P_{scan}$, from $P_{scan,min}$ to $P_{max}$, where $P_{scan,min}$ is less than $P_{max}$, and $P_{max}$ is the maximum allowed light source output intensity. The method may further comprise the step of decrementing the output intensity of the light source via a power scanning step, the power scanning step allowing for decrementing the output intensity of the light source a few times with a specified step $\Delta P_{scan}$, from $P_{scan,max}$ to $P_{min}$, where $P_{scan,max}$ is greater than $P_{min}$, and $P_{min}$ is the minimum allowed light source output intensity.

Other objects of the invention are achieved by providing an apparatus for viewing a surface comprising: an examining instrument, the examining instrument having an imaging path through which the surface is observed; a light source, the light source illuminating the surface; an imager, the imager detecting light reflected from the surface, and generating image signals; a camera control unit (CCU), the CCU processing the image signals; and a controller associated with the imager and CCU.

The controller of the apparatus may decrement or increment the intensity of the light source output via a plurality of steps. The intensity of the at least two steps and/or plurality of steps may be incremented or decremented in intervals as small as 1% of the total light source intensity output. The power intervals incremented or decremented may be in steps that are greater than 1% (i.e. 3%, 5%, 15%) or in steps less than 1% (i.e. 0.25%, 0.5%) of the total light source output intensity; depending upon the operational characteristics of the light source, camera head/imager, CCU, and other devices being utilized. The magnitude of the at least two steps may be incremented or decremented by a predetermined percentage of the maximum light source output intensity.

Other objects of the invention are achieved by providing an apparatus for viewing a surface comprising: an examining instrument, the examining instrument having an imaging path through which the surface is observed; a light source, the light source illuminating the surface; a CMOS imager, the CMOS imager detecting light reflected from the surface, and generating image signals; a camera control unit (CCU), the CCU processing the image signals; and a controller associated with the CMOS imager and CCU, the controller decrementing or incrementing the intensity of the light source output via predetermined steps.

Other objects of the invention are achieved by providing a method for protection from a high intensity light source output comprising: measuring an exposure value $EV_{meas}$, $EV_{meas}$ being used to control the intensity of the light source output; and incrementing or decrementing the output intensity of the light source $P_{scan}$ based upon the exposure value $EV_{meas}$; determining an optimal value of $EV_{meas}$, which is $EV_{opt}$, $EV_{opt}$ being between $EV_{opt,min}$ and $EV_{opt,max}$, and $EV_{opt}$ being dependent on the monotonic and linearity characteristics of the light source, wherein if $EV_{meas}$ is less than $EV_{opt,min}$, the output intensity is incremented, wherein if $EV_{meas}$ is greater than $EV_{opt,max}$, the output intensity is decremented, and wherein if $EV_{meas}$ is between $EV_{opt,min}$ and $EV_{opt,max}$, the output intensity is unchanged.

Other objects of the invention are achieved by providing an apparatus for protection from a high intensity endoscopic light source output comprising: an endoscope having an imaging path through which the surface at a distal end can be observed; a Xenon light source for illumination of the surface; an imager detecting light reflected from the surface and generating image signals; a camera control unit (CCU) processing the image signals received from the imager, the camera control unit including a controller, the controller being able to increment or decrement the output intensity of the Xenon light source, such that if the controller detects a potential safety issue, the Xenon light source output intensity is adjusted via at least one discrete step $\Delta P_{scan}$, from $P_{min}$ to $P_{max}$, where $P_{scan,min}$ is less than $P_{max}$, and $P_{max}$ is the maximum allowed light source output intensity; and a communication bus coupled to a plurality of bus interfaces for communication between the Xenon light source and the camera control unit.

Other objects of the invention are achieved by providing an apparatus for protection from a high intensity endoscopic light source output comprising: an endoscope having an imaging path through which the surface at a distal end can be observed; a light source for illumination of the surface; a camera head including an image sensor aligned to detect light reflected from the surface and for generating image signals; a camera control unit processing the image signals received from the camera head, the camera control unit including a controller associated with the camera head to process image signals representative of images detected by the image sensor, the controller being able to increment or decrement the intensity of the light source output; and a communication bus coupled to a plurality of bus interfaces for communication between the light source and the camera control unit.

The apparatus may have its controller include an exposure value $EV_i$ (i.e. the shutter speed), $EV_i$ being used to control the output intensity of the light source. The apparatus may measure the value $EV_i$, referred to as $EV_{meas}$. When $EV_{meas}$ is below a threshold $EV_{tr}$, the light source output intensity $P_{rec,i}$ may be reduced. This is to prevent the overheating or burning of tissue due to a small distance between the distal end of the endoscope or videoscope apparatus and the observed tissue.

The apparatus may have an optimal value of $EV_i$, $EV_{opt}$, which may be between $EV_{opt,min}$ and $EV_{opt,max}$, wherein $EV_{opt}$ depends on $EV_{meas}$, the monotonic and linearity characteristics of the light source output. The criteria to form well-exposed images requires that $EV_{meas}$ be between $EV_{opt,min}$ and $EV_{opt,max}$. Thus, it is advantageous to keep $EV_{meas}$ within this range so that well-exposed images are created.

If $EV_i$ or $EV_{meas}$ is less than $EV_{opt,min}$, the light source output $P_{rec,i}$ is incremented, if $EV_i$ or $EV_{meas}$ is greater than $EV_{opt,max}$, the light source output $P_{rec,i}$ is decremented, and if $EV_i$ is between $EV_{opt,min}$ and $EV_{opt,max}$, the light source output is unchanged. This controls the light source output via increments/decrements and helps keep the light source output intensity at a safe level while minimizing number of changes of output intensity.

The apparatus minimizes the number of increments or decrements of $P_{rec,i}$, so as to keep the light source output intensity at a safe level. Minimizing the number of increments or decrements $P_{rec,i}$ allows the apparatus to operate more efficiently and accurately.

The apparatus may have a scan request method. The scan request method is able to detect a potential safety issue. The potential safety issue may involve having the light source output intensity exceed $P_{max}$. Once the potential safety issue is detected by the scan request method, power scan method and correlation method may be enabled, and EV method may be disabled.

The power scan method may be able to increment the output intensity a few times with a specified step $\Delta P_{scan}$, from $P_{scan,min}$ to $P_{max}$, where $P_{scan,min}$ is less than $P_{max}$, and $P_{max}$ is the maximum allowed light source output intensity. The power scan method may be able to decrement the output intensity a few times with a specified step $\Delta P_{scan}$, from $P_{scan,max}$ to $P_{scan,min}$.

The scan request method may further involve a correlation method running simultaneously with the scan method and allowing for computation of correlation (i.e., dependence) between the incrementing output intensity and the light intensity reflected from tissue or observed surface. Absence of such dependency, i.e., absence of computed correlation may be used to detect when light source output is not directed to a surface and to lower the output intensity of the light source to a safe level.

The apparatus may have the intensity of its light source output be automatically reduced to a safe level when the light source output is not directed at a surface.

The apparatus may have its controller include a method to detect disconnection of the camera head, image sensor, and light source. The apparatus may have the intensity of its light source be automatically reduced to a safe level when at least one of the camera head, image sensor, and light source output are disconnected.

The apparatus may have its controller include adaptive normalization and self-calibration. Adaptive normalization may include normalizing of exposure value EV. The self-calibration may have the capability to recompute calibration curves based on the type of light source and/or the camera head/imager being used. The adaptive normalization and self-calibration may depend on imager integration time $T_{int}$, $EV_{min}$ and $EV_{max}$. Moreover, the apparatus may include methods in its controller to detect when the light guide/source is disconnected, when the camera is disconnected, and when no motion is detected in the video images. Such a method (failure-detection method) may be based on a comparison of achromatic image brightness (Luma), Perimeter Black (PB) and Image Motion Metrics (IMM) with their corresponding thresholds, i.e., $Luma_{tr}$, $PB_{tr}$, and $IMM_{tr}$, respectively.

The apparatus may have its controller include the self-recovery method. This involves adaptive normalization and self-calibration when components in the system are changed during use and/or surgery. Components that are replaced and/or changed are the type of scope attached to the camera, the light source, camera, videoscopes, endoscopes and/or CCU. Other components in the system may also be replaced.

The self-recovery method may protect from possible failure of LSC caused by the new and/or replacement components during surgery.

The controller of the apparatus may or may not be continuously enabled, so as to minimize possible flickering of the video images. The apparatus may include a control feature that involves single code-implementation, without having hardware changes. The apparatus may be reconfigured with this single code-implementation, as the apparatus may utilize an existing endoscope.

Other objects of the invention are achieved by providing a method for protection from the output of high intensity light sources comprising: measuring an exposure value $EV_i$, $EV_i$ being used to control the output intensity of the light source; and adjusting the output intensity of the light source based upon the $EV_i$.

The measured $EV_i$ may be $EV_{meas}$, and when $EV_{meas}$ is below the threshold $EV_{tr}$, the light source output intensity may be reduced. This is known as a step of the detection of the hot distal end of the endoscope, as when $EV_{meas}$ is less than $EV_{tr}$ then the tissue is too close to the distal end of the endoscope and the light source output intensity is lowered to avoid high temperature at the distal end that may cause the tissue to burn.

The method may also have a failure detection method or may have failure detection steps. This may involve decreasing the light source output intensity to a safe level when the light source is disconnected, when the camera and/or light-guide is disconnected from the endoscope, and when there is no motion detected in the video images. The failure detection methods may be based on comparison of achromatic image brightness (Luma), Perimeter Black (PB) and Image Motion Metrics (IMM) with their corresponding thresholds, i.e., $Luma_{tr}$, $PB_{tr}$, and $IMM_{tr}$, respectively. When $Luma_{meas}$ is less than $Luma_{tr}$, either low or no light is detected by the imager; therefore, the light guide/source is possibly either disconnected from the endoscope or endoscope/camera combination, the distal tip of the endoscope is not within close enough proximity to a subject being imaged to produce well exposed images (i.e., reflected light levels are below the Luma threshold, indicative of the endoscope being too far from the imaged subject to be "in use"), and the power is decreased to a safe level. When $PB_{meas}$ is less than $PB_{tr}$, the camera may be disconnected from the endoscope and the power is decreased to a safe level. When $IMM_{meas}$ is less than $IMM_{tr}$, motion is not detected within the video images, indicative of the endoscope or endoscope/camera combination being static (i.e., not being actively used for a surgical procedure); therefore, the light source output is decreased to a safe level.

The method may also have an exposure value step and/or method. The goal of the exposure value step and/or method is to minimize the number of power changes (increment or decrement) taking into account known issues with Xenon light sources.

The exposure value step may involve having the optimal value of $EV_i$, $EV_{opt}$, be between $EV_{opt,min}$ and $EV_{opt,max}$, wherein $EV_{opt}$ depends on the monotonic and linearity characteristics of the light source. If $EV_i$ is less than $EV_{opt,min}$, the output intensity of the light source is incremented, if $EV_i$ is greater than $EV_{opt,max}$, the output intensity of the light source is decremented, and if $EV_i$ is between $EV_{opt,min}$ and $EV_{opt,max}$, the output intensity of the light source is unchanged. The criteria to produce well-exposed images may require that $EV_{meas}$ be between $EV_{opt,min}$ and $EV_{opt,max}$. The $EV_{meas}$ may be a continuously measured exposure value $EV_i$.

To compensate for the ineffectiveness of using an output modulation method with Xenon or Xenon-like light sources, the controller may compute a correlation metric between illuminating and reflected light only when $EV_{meas}$ is too high, i.e., when $P_i$ is requested to be around $P_{max}$ or higher (where $P_{max}$ is the maximum output intensity of the light source). While computing the correlation-metric, instead of light-modulation, one or a few sets of incrementing output intensity levels are requested: each set produces a ramp of increasing light source output levels. This allows the present method to be effective for light sources that have slow-response, high-frequency noise, nonlinearity, non-monotonic response times, such as with Xenon based light sources.

One goal of the exposure value method minimizes the number of output intensity level changes and avoids loops in output level requests (i.e., avoids instability of the output-control loop when the controller wrongfully requests periodical increment/decrement of output intensity).

Another goal of the exposure value method is to increase the accuracy of computing correlation and minimize the number of such computations, and as a result, minimize the number of changes in light source output intensity.

The method may also involve adaptive normalization and self-calibration method steps. The adaptive normalization and self-calibration method steps take into account the type of the imager (i.e., video endoscope or camera head) connected to the CCU, and the type of light source. The method may also involve a delay block to compensate for the slow response of Xenon or Xenon-like light sources by using optimal delays before and/or after controlling of the light source output.

The adaptive normalization and self-calibration method steps normalize EV to the imager being used in order to reuse the same control-equations, and re-computes calibration curves based on the type of imager and light source being used. The adaptive normalization and self-calibration method steps monitor the imager integration time $T_{int}$, minimum exposure value $EV_{min}$ and the maximum exposure value $EV_{max}$ values of EV.

The method may also include steps of the self-recovery method. The self-recovery method may work, such that when equipment is changed, the previously used processing coefficients, equations, and/or calibration curves are no longer valid.

The self-recovery method adaptive normalization and self-calibration when components in the system are changed during use and/or surgery. Components that are replaced and/or changed are the type of scope attached to the camera, the light source, the camera, videoscopes, endoscopes and/or the CCU. Other components in the system may also be replaced.

The self-recovery method may protect from possible failure of LSC caused by the new and/or replacement components during surgery.

Other objects of the invention are achieved by providing a method and apparatus that uses an exposure value (EV) to minimize the number of increments or decrements of light intensity output taking into account known issues with Xenon light sources. The exposure value denotes all combinations of a camera's shutter speed and relative optical aperture that result in the same exposure.

Other objects of the invention allow for the controller to be wirelessly controlled. Other objects of the invention allow for the controller to incrementally change the intensity of the light source. Other objects of the invention allow for the intensity of the light source to be changed so as to optimize the image quality while ensuring the light source output intensity remains at a safe level.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 1B is a schematic block diagram view of the methods for controlling the controller of FIG. 1;

DETAILED DESCRIPTION OF THE INVENTION

Figure 1:
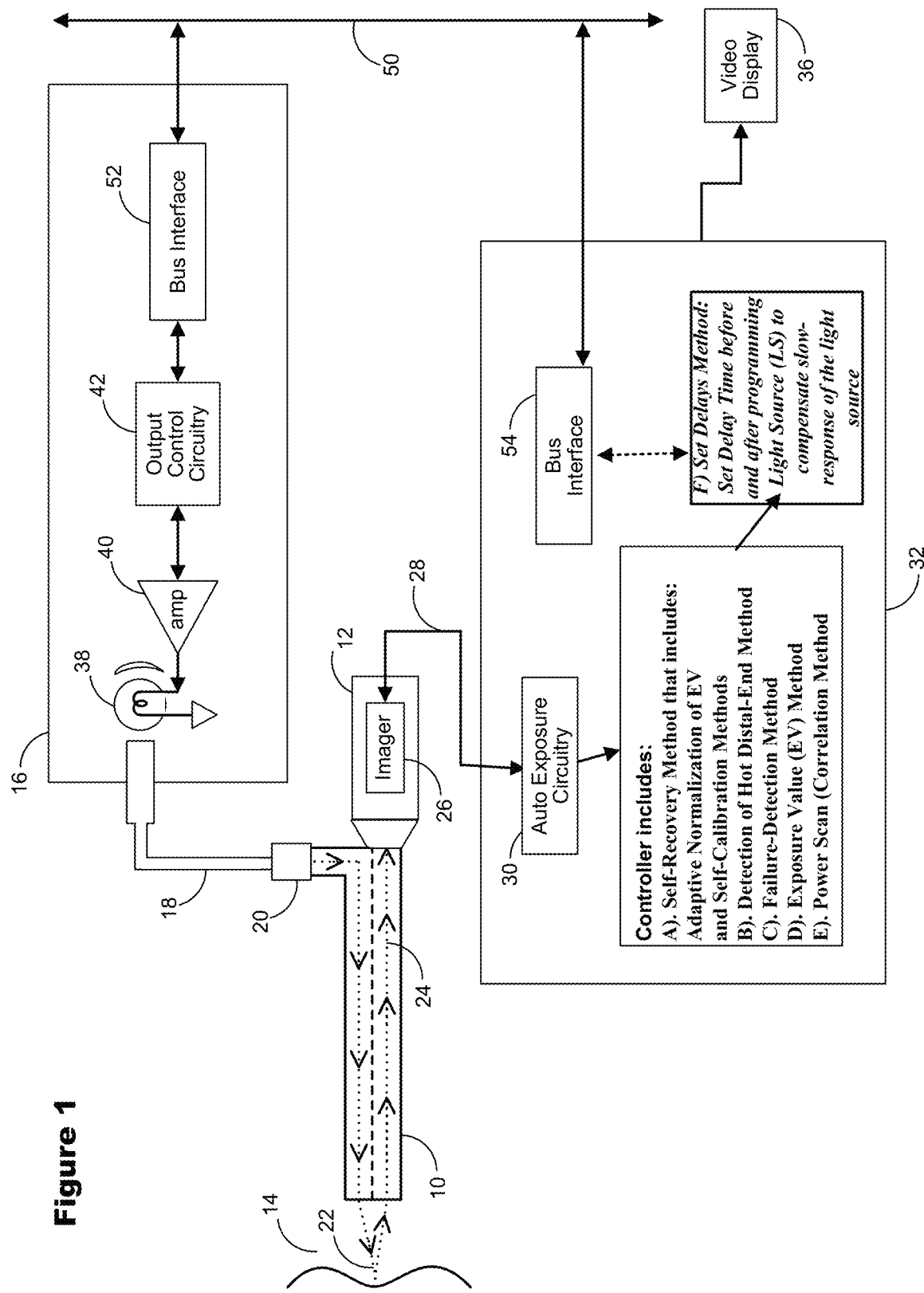
FIG. 1 is schematic block diagram view of an apparatus for controlling a light source in accordance with the invention.

With reference to FIG. 1, an endoscope 10 is illustrated having a camera head 12 mounted thereto at the proximal end to produce video images in a manner for example as described in the aforementioned U.S. Pat. No. 5,162,913 to Chatenever, et al. The distal end of endoscope 10 is directed at tissue 14 to inspect the tissue with light from a high intensity light source 16 and passed to the distal end through a light guide cable 18. Typically, light guide cable 18 can be disconnected from endoscope 10 at connector 20, thus, posing a safety hazard as described above.

The light from light guide cable 20 is directed to illuminate tissue 14 as suggested with path 22 and light reflected by tissue 14 is passed along optical path 24 to imager 26 within camera head 12. Imager 26 detects light reflected off tissue 14 by means of optical path 24. Imager 26 may be any type commonly used within the art, such as but not limited to CCD, CID or CMOS imagers. Camera head 12 produces image signals 28, which are received by auto exposure circuitry 30, within camera control unit (CCU) 32. Auto exposure circuitry 30 may consist of various types of methods for controlling the electronic shutter of imager 26, as well as adjusting amplification gain in response to illumination levels received by imager 26. Typically, within the field of video endoscopy, auto exposure circuitry has high-speed and wide dynamic range capabilities. Various methods may be utilized, that are well known within the art. Video display 36, receives signals from CCU 32, where an image of tissue 14 is presented.

As shown in FIG. 1, light source 16 is controlled by CCU 32 and controller 234, by means of CCU bus interface 54, digital communication bus 50, and light source bus interface 52. Controller 234, may be any type of device designed to receive and execute software programs, or which is designed to be modified in functionality by software programs, and preferably is from the group consisting of digital signal processors, microcontrollers, and microprocessors, or the group consisting of field programmable gate arrays, and computer programmable logic devices.

Typically, high intensity light sources utilize an incandescent bulb 38 (being a Xenon bulb, or other type), driven by an amplifier 40, which in turn is controlled by output control circuitry 42, to set the light output intensity level of the light source 16. Other types of light source intensity output control are known within the art; such as mechanical diaphragm or iris, liquid crystal shutter, rotary reed or slot devices, and the like. These various types of light source output intensity control may be utilized within the scope of the present invention. In the present embodiment, output control circuitry 42 varies the intensity of bulb 38 in accordance with controller 234.

Figure 1A:
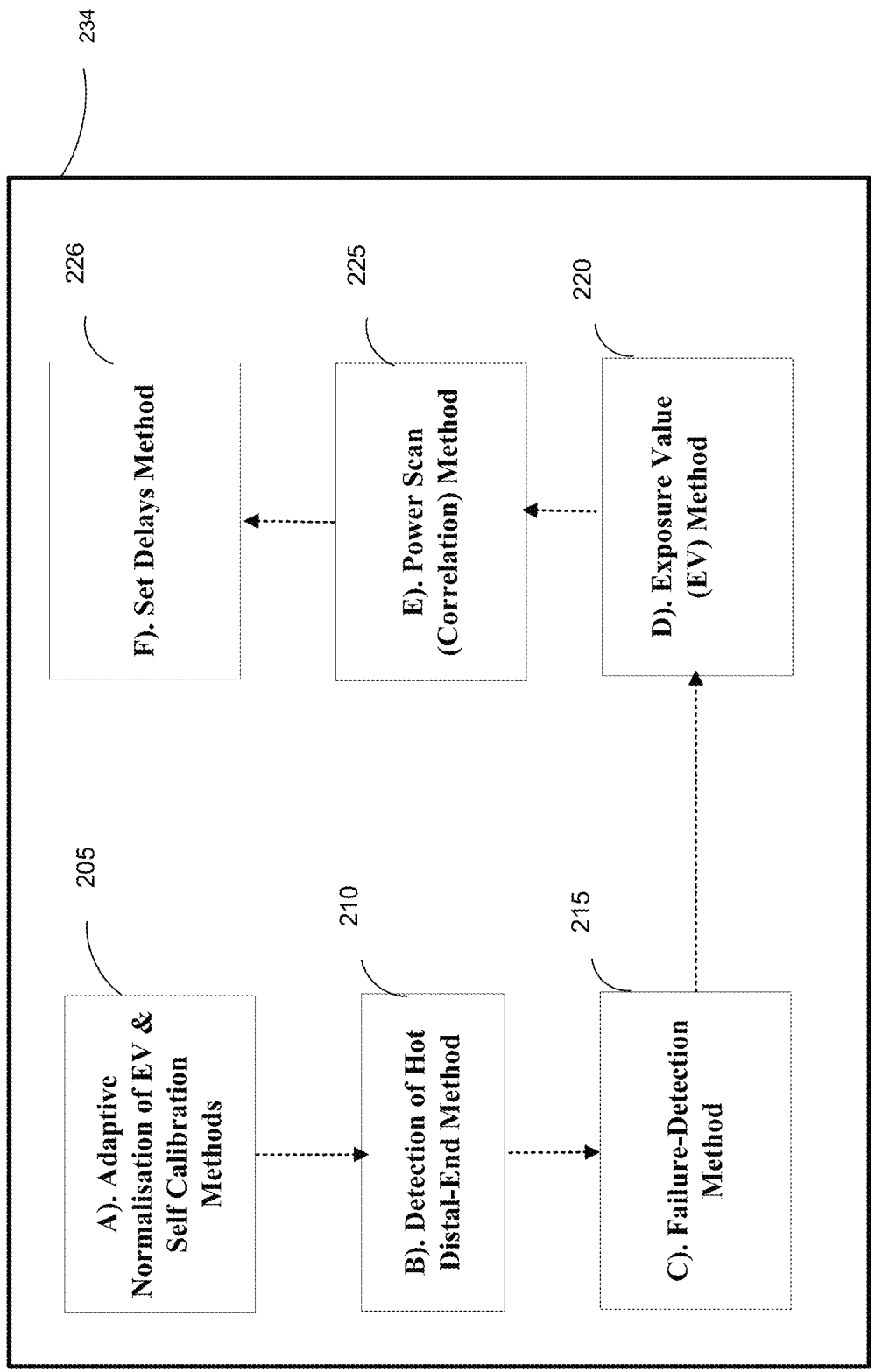
FIG. 1A is schematic block diagram view of the controller of FIG. 1.

Controller 234 is a modified controller that is used to achieve the various objects of the invention. As shown in FIG. 1, controller 234 involves various steps A-F that allow the apparatus to control light sources that have slow-response, high-frequency noise, nonlinearity, non-monotonic response times. Controller 234 may have steps A) Adaptive Normalization of EV and Self Calibration 205, B) Detection of Hot Distal-End Method 210, C) Failure-Detection Method 215, D) Exposure Value Method 220, E) Power Scan and Correlation Methods 225 and F) Set Delays Method 226. Such steps are shown in FIG. 1A. FIG. 1B shows steps for the Scan Request 230, Power Scan 235, and Correlation 240. Scan Request 230, Power Scan 235, and Correlation 240 are part of the Power Scan and Correlation Method 225.

Figure 3:
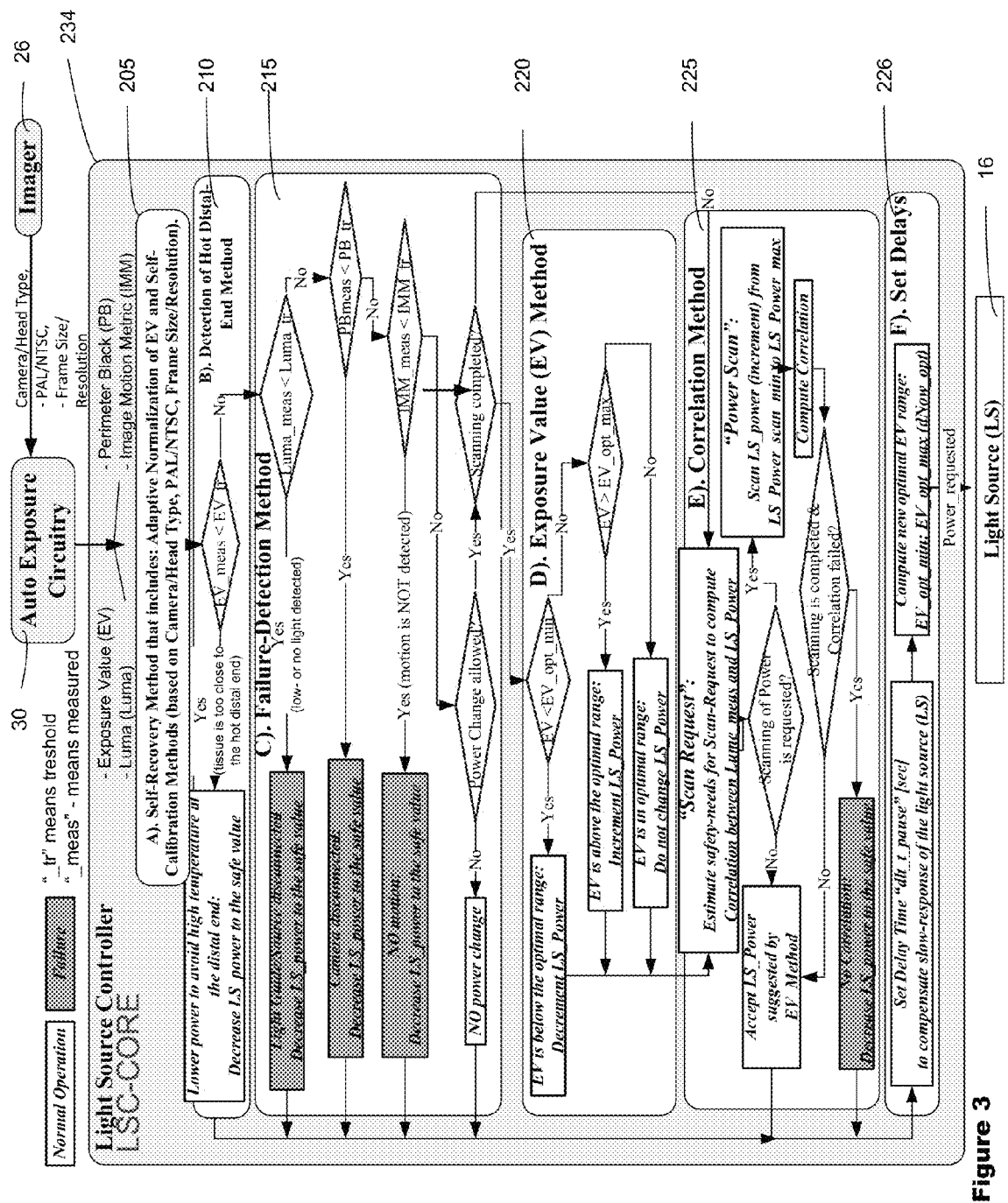
FIG. 3 is a schematic view of the steps of controlling the controller of FIG. 1.
Figure 3A:
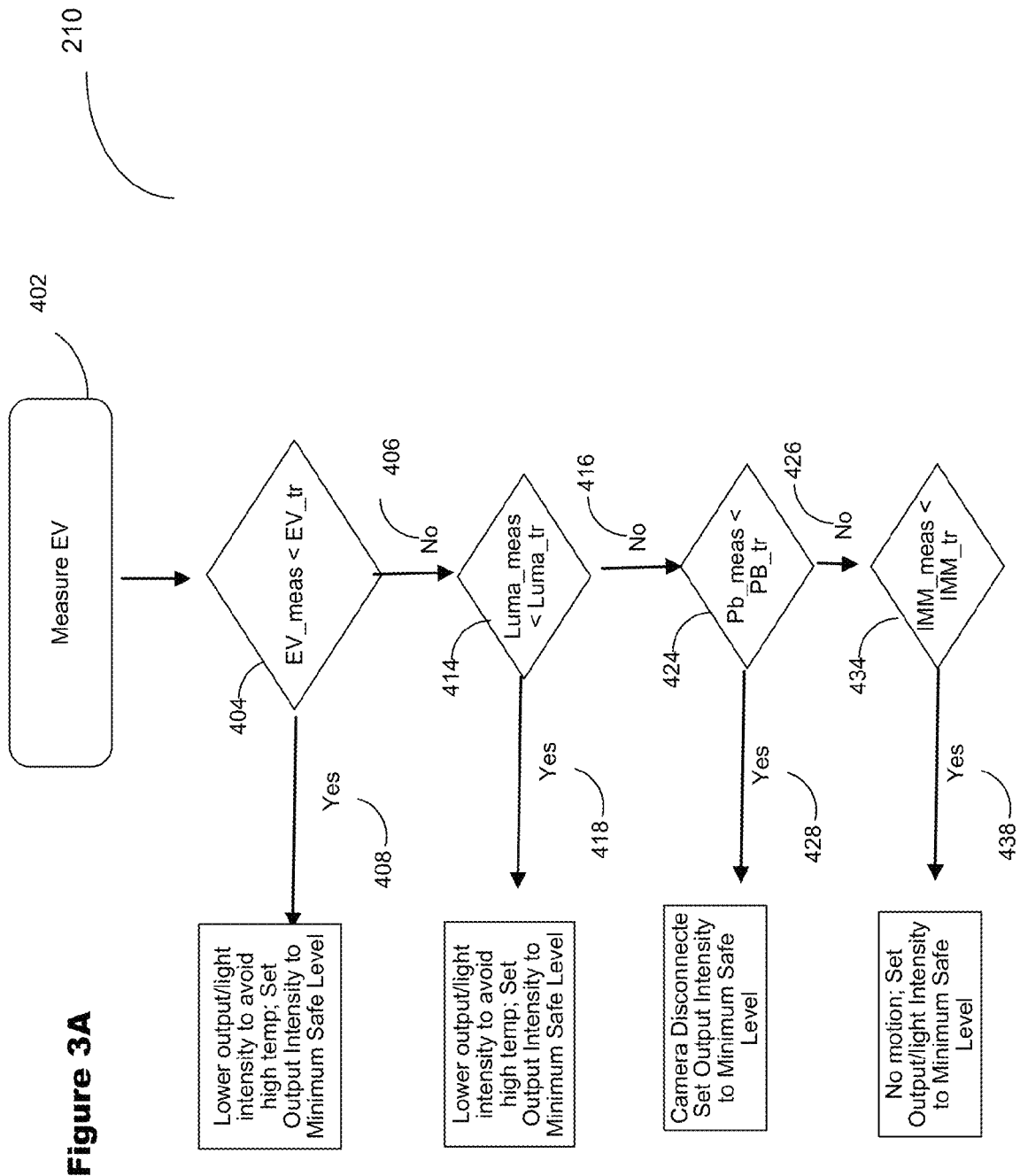
FIG. 3A is a schematic block diagram view of some of the steps of FIG. 3.
Figure 3B:
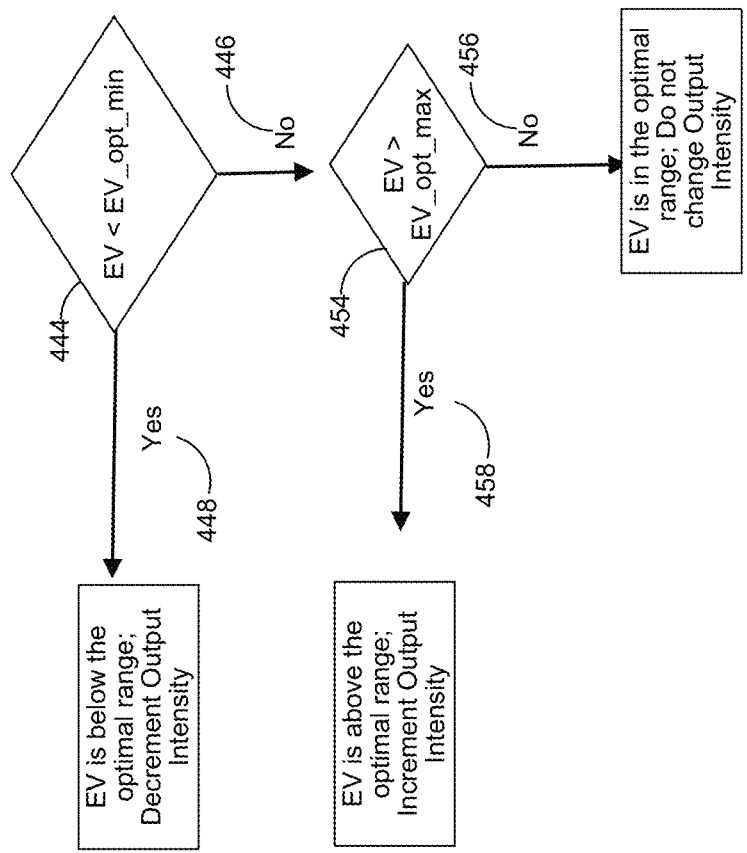
FIG. 3B is a schematic block diagram view of some of the steps of FIG. 3.

FIG. 3 shows a global schematic view of the steps of the controller 234. FIG. 3A-3B show steps of FIG. 3.

The step 210 is the Detection of Hot Distal-End Method. Here, the step 210 measures EV 402 and checks to see if $EV_{meas}$ is less than the threshold $EV_{tr}$ 404. If yes 408, then the tissue is too close to the hot distal end and the light source intensity is reduced by lowering the output intensity to avoid high temperature at the distal end. The output intensity is decreased to a safe value, as when $EV_{meas}$ is less than $EV_{tr}$, then the tissue is too close to the distal end of the endoscope and the output intensity is lowered to avoid high temperature at the distal end that may cause the tissue to burn.

Next, Failure-Detection Method step 215 is provided. Here, the method checks to see if $Luma_{meas}$ is less than $Luma_{tr}$ 414. If yes 418, this indicates that low or no light is detected by the camera; therefore, the light guide/source is possibly either disconnected from the endoscope or endoscope/camera combination, the distal tip of the endoscope is not within close enough proximity to a subject being imaged to produce well exposed images (i.e., reflected light levels are below the Luma threshold, indicative of the endoscope being too far from the imaged subject to be "in use"), Thus, the output intensity is decreased to a safe level. If no 416, then the method checks whether $PB_{meas}$ is less than $PB_{tr}$ 424. Perimeter Black (PB) is typical in endoscope images. Endoscopes generally provide a circular image of the tissue being examined in the middle of the overall image, surrounded by a black perimeter extending to the square or rectangular edges of the overall image. The Perimeter Black (PB) being absent in the image (i.e., $PB_{meas}$ is less than $PB_{tr}$) is indicative of the camera being disconnected from the endoscope. Therefore, if yes 428, then the camera is disconnected and the output intensity is decreased to a safe level. If no 426, then the system checks whether $IMM_{meas}$ is less than $IMM_{tr}$ 434. If yes 438, then motion is not detected within the video images and the output is decreased to a safe level. If no, then the Controller checks to see if an output level change is allowed. If no output change is allowed (no), then the light source output level is unchanged. If an output change is allowed (yes), then the Controller checks if Scanning of Power (light output intensity) is complete. If Power Scan is completed, the Exposure Method EV is allowed/enabled. If Power Scan is not completed, EV method is disabled while Power Scan and Correlation methods are enabled. The next step involves the Exposure Value Method 220 if EV method is enabled. The exposure value method involves having the optimal value of $EV_i$, $EV_{opt}$, be between $EV_{opt,min}$ and $EV_{opt,max}$, wherein $EV_{opt}$ depends on the monotonic and linearity characteristics of the light source.

The exposure value method 220 first checks to see if $EV_i$ is less than $EV_{opt,min}$ 444. If yes 448, then EV is below the optimal range and the output level of the light source is decremented. If no 446, next the method checks to see if $EV_i$ is greater than $EV_{opt,max}$ 454. If yes 458, then EV is above the optimal range and the output level of the light source is incremented. If no 456 then, EV is in the optimal range ($EV_i$ is between $EV_{opt,min}$ and $EV_{opt,max}$) and the output level of the light source is unchanged. The criteria to form a well-exposed image typically requires that $EV_{meas}$ be between $EV_{opt,min}$ and $EV_{opt,max}$. The $EV_{meas}$ is continuously measured exposure value EV. The $EV_{opt}$ depends on $EV_{meas}$, the monotonic and linearity characteristics of the light source output.

The absence of intensity is compensated by increasing of EV in the CCU/imager that is measured ($EV_{meas}$) for the LSC. The larger the $EV_{meas}$, the worse quality of the image because the image is under exposed. To improve quality of the image, the intensity is increased. Thus, when $EV_{meas}$ is greater than $EV_{opt,max}$ (where $EV_{opt,max}$ is the upper range of the optimal window for $EV_{meas}$), LSC requests increasing the light intensity.

When the end of the scope is touched by the patient tissue/surface, EV will be reduced by CCU to prevent from overexposure (when image is one bright spot). As shown in FIG. 3, 3A and 3B, LSC helps the CCU/imager by decreasing light intensity when CCU reduces EV.

In other words, the LSC helps the CCU/imager keep $EV_{meas}$ in the optimal range, i.e., EV shall not be too big (by incrementing the intensity) and EV shall not be too small (by decrementing the intensity).

The goal of the exposure value step and/or method is to minimize the number of light source output level changes (increment or decrement) taking into account known issues with Xenon light sources.

The goal of the exposure value method 220 is to minimize the number of output intensity level changes and avoid loops in output intensity requests (i.e., avoids instability of the output intensity control loop when the controller wrongfully requests periodical increment/decrement of output). Another goal of the exposure value method 220 is to increase the accuracy of computing correlation and minimize the number of such computations, and as a result, to minimize the number of changes of light source output intensity.

The next step is power scan step 225, which involves scan request step 230, power scan step 235 and if requested, correlation step 240. These steps allow for the incrementing of the output intensity of the light source. Here, the output intensity of the light source may be incremented via the power scan step 225, power scan step 225 being able to increment the output intensity a few times with a specified step $\Delta P_{scan}$, from $P_{scan,min}$ to $P_{max}$, where $P_{scan}$ is less than $P_{max}$, and $P_{max}$ is the maximum allowed light source output intensity. The above mentioned step is typically not continuously enabled to minimize possible flickering of the video images. The next step is Set Delays method 226 to compensate for the slow response of Xenon or Xenon-like light sources by using optimal delays before and/or after controlling of light source.

The correlation method may compute a correlation metric when $EV_{meas}$ is too small, i.e., when $P_i$ is requested to be around $P_{max}$ or higher (where $P_{max}$ is the maximum output level of the operating light source). While computing the correlation metric, instead of light-modulation, one or a few sets of incrementing intensity output levels are requested: each set producing a ramp of increasing light output intensity.

Figure 2:
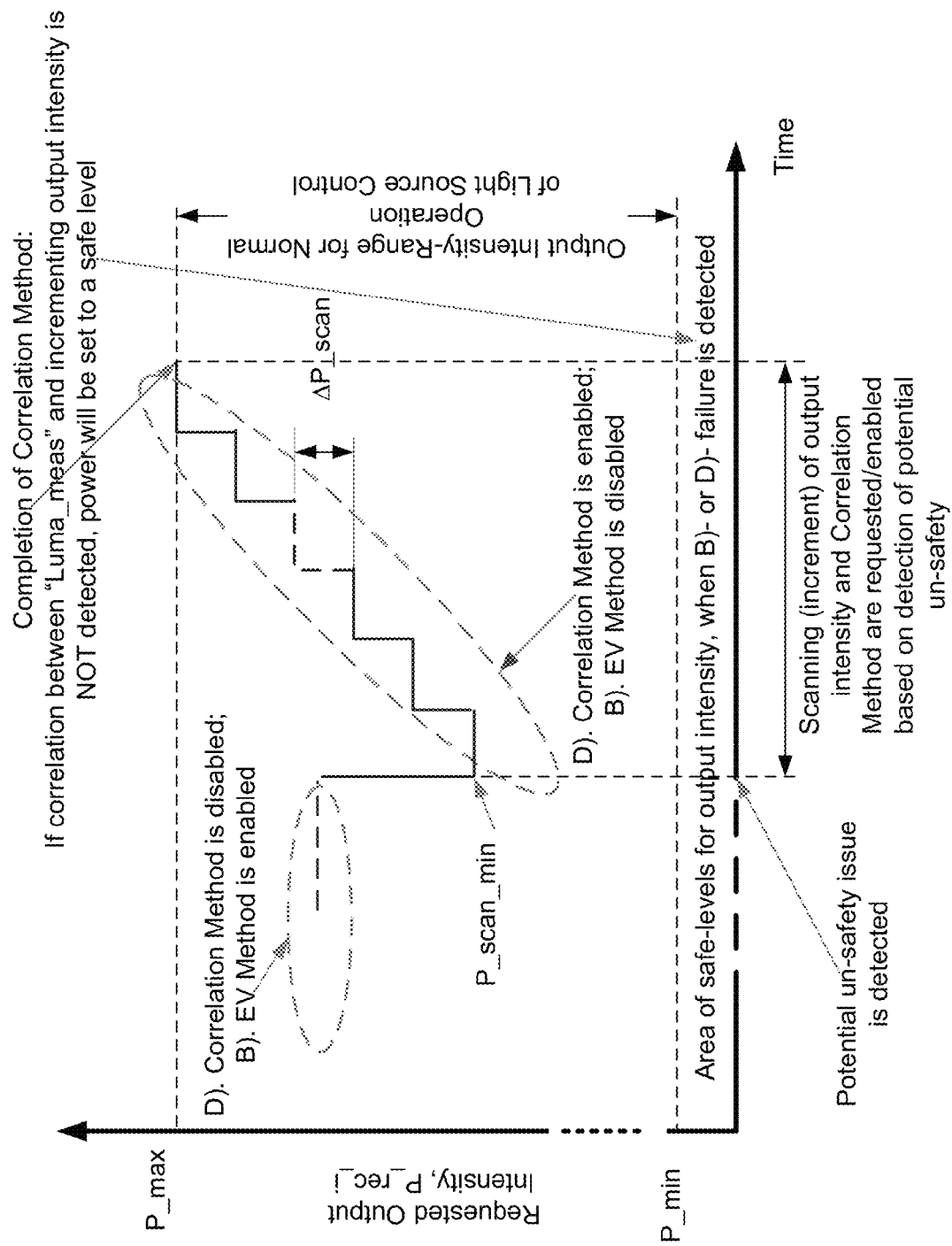
FIG. 2 is a graph comparing requested output intensity of light source against time that shows incrementing and decrementing the power in a stepwise manner.

FIG. 2 is a graph of the power scan step 225. Here, the graph shows regions where the correlation method is enabled or disabled and where there is a safe intensity output level.

As shown in the graph, where the correlation method is enabled and the EV method is disabled, the output intensity can be incremented. The output intensity can be incremented via steps from $P_{scan,min}$ to $P_{max}$, and vice-versa. Optionally, the output intensity may be decremented via steps from $P_{max}$ to $P_{scan,min}$. When a potentially unsafe condition is detected, the correlation method is enabled and the EV method is disabled. On the right hand side of the graph, upon completion of the correlation method one or more times, if the correlation between $Luma_{meas}$ and incrementing output level is not detected, the output intensity may be set to a safe level.

The method may also involve adaptive normalization and self-calibration method steps. The adaptive normalization and self-calibration method steps take into account the type of the imager (i.e., video endoscope or camera head), connected to the CCU, and the type of light source.

The adaptive normalization and self-calibration method steps may normalize EV to the imager being used in order to utilize a single LSC software implementation, to reuse the same control-equations, and to re-compute calibration curves based on the type of imager and light source. The adaptive normalization and self-calibration method steps may monitor the integration time of the imager, and the minimum and maximum values of $EV_i$.

The adaptive normalization and exposure value methods may take into account the type of imager (i.e., camera and camera head) connected to the CCU, including imager format (i.e. PAL, NTSC, SECAM, etc.) resolution, (i.e. frame size or field size for interlaced imagers), and type of light source. The method may adaptively normalize $EV_i$ to the imager being used, in order to re-use the same control equations, the same control-thresholds, and a single LSC software implementation and/or package for all imagers and re-computes calibration curves based on the type of imager and light source.

The adaptive normalization and self-calibration methods may also include steps for the self-recovery method. The self-recovery method involves, such that when components of the system are changed, updating the previously used processing coefficients, equations, and/or calibration curves associated with the previous components. These processing coefficients, equations, and/or calibration curves associated with the previous components are no longer valid or accurate when components of the system are changed. Keeping these old values could lead to a wrong computation of a new safety level.

When components in the system are changed, the self-recovery method automatically fixes the above issue by re-computing the coefficients, equations and calibration curves taking into account new correct equations and/or Look Up-Tables in order to compute the safe power-level correctly. In other words, the self-recovery method works as auto-adaptive method that allows for high-accuracy of computation of a safe power level or output intensity level during the change of components and/or equipment in a system.

Components that are replaced and/or changed are the type of scope attached to the camera, the light source, the camera, any endoscopes, videoscopes and/or CCU.

As an example using the self-recovery method, the LSC implemented from GI-CUU and Image-1 HD CCU can self-recover when a type of the scope/light source is changed (for example, when 10 mm scope is replaced with 5 mm scope; or when Xenon-300 is replaced with Power LED light source during the surgery).

Furthermore, the self-recovery method may be incorporated into other operative methods of the system and/or method of the invention.

Figure 4:
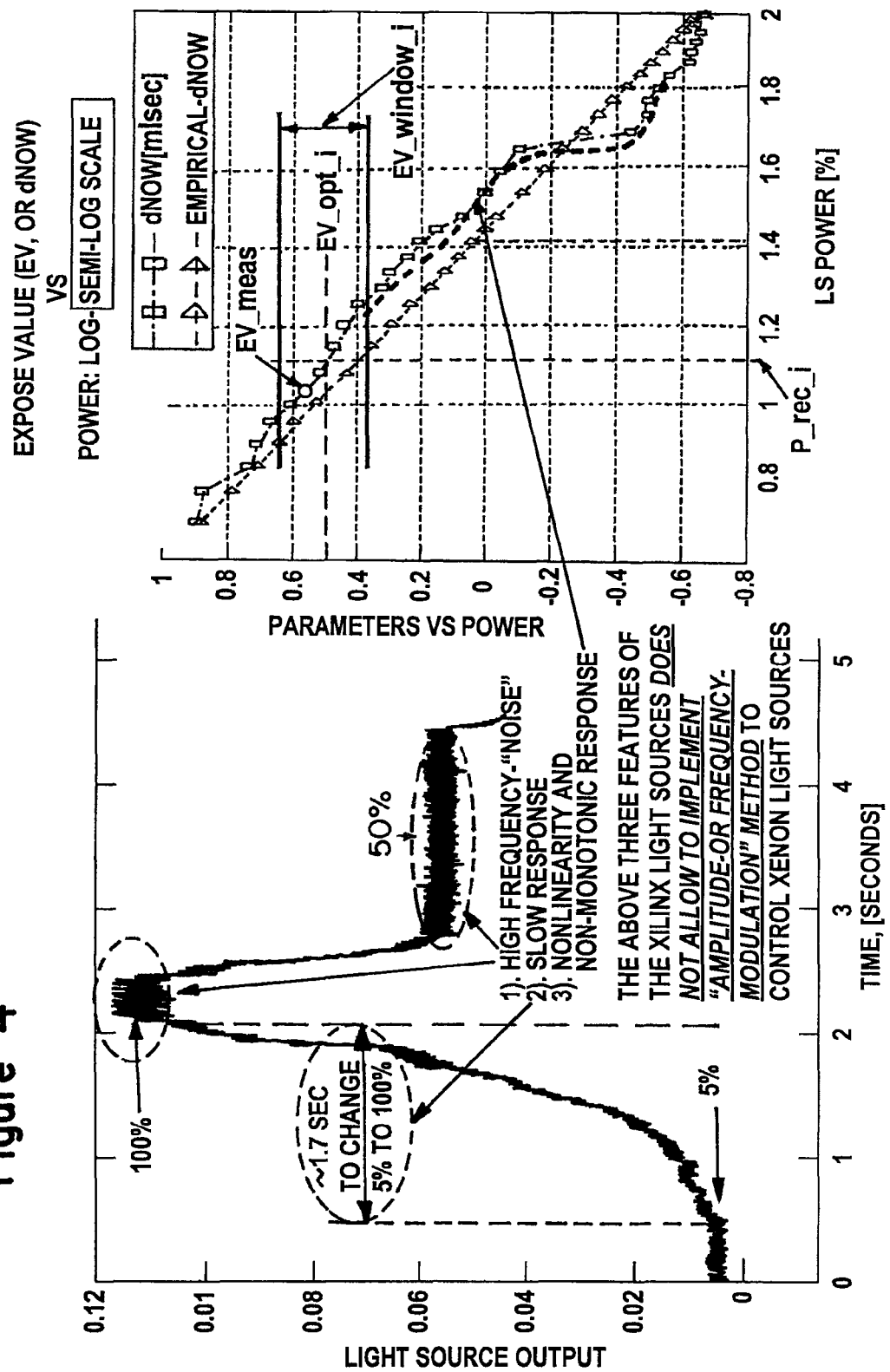
FIG. 4 is a graph showing the high frequency noise, slow-response and nonlinearity of a Xenon or a Xenon-like light source and comparing the output intensity of a Xenon or a light source against time.

The method and apparatus of the present invention has advantages over existing systems. As shown in FIG. 4, the method overcomes slow-response, high-frequency noise, nonlinearity, and non-monotonic response features of Xenon light sources and light sources similar to Xenon sources.

FIG. 4 shows a time versus light source output graph illustrating high-frequency noise, as well as slow-response (more than a second to change light source output intensity from 5% to 100%). On the right, FIG. 4 shows an exposure value EV versus output intensity graph on a semi-log scale demonstrating the nonlinearlity and non-monotonic response of Xenon based light sources. These features (i.e., the slow-response, high-frequency noise, nonlinearity, and non-monotonic response features of Xenon light sources) do not allow control methods involving any type of modulation (such as described in U.S. Pat. No. 6,511,422 to Chatenever) to satisfactorily control Xenon light source outputs.

The present invention may also operate to prevent fire hazard through light guide disconnection and to minimize light source intensity output in-vivo to minimize tissue burn. The present invention may also provide eye safety, and detection of camera and/or light guide disconnection. The invention achieves a single software package that does not impact existing hardware.

The controller of the present apparatus takes into account the exposure value (i.e., the shutter speed in seconds). The invention may also provide a correlator that is a part of the controller.

The invention may also involve providing software packages that do not impact existing algorithms for power control. The invention also supports various imager formats (i.e. NTSC, PAL, SECAM, etc.), as well as varying resolutions, frame and field sizes as in interlaced imagers. The hot distal end method step may involve checking if measured exposure value $EV_{meas}$ is below the threshold $EV_{tr}$ and if so the light source intensity is immediately reduced to prevent overheating/burning of tissue due to the small distance between the distal end of the scope and the observed tissue.

The failure-detection method may include methods to detect the following failures to reduce the light source intensity to a safe level: light guide/source disconnect, camera disconnect, and detection of no movement within the video image. This may be based upon comparison of measured Luma, Perimeter Black (PB), and Image motion metrics (IMM) with corresponding thresholds, i.e., $Luma_{tr}$, $PB_{tr}$ and $IMM_{tr}$.

The design style/workflow for the method for LSC may involve an effective and fast-to-market style, such as the style provided in http://www.mil-embedded.com/articles/id/?4881, an article by Joy Lin, entitled "Developing next-gen signal processing and communications systems: Engineering tools and design flow advancements", which is herein incorporated by reference. As an example the Model-Based design workflow may involve various Matlab tools for design, test and verification of LSC, and for one-button push conversion of the proved Matlab LSC code into the corresponding C/C++/VHDL/Verilog-code for hard/firm-ware implementation. This allows fast-to-market of the reusable LSC design and prospective upgrades, changes, or modification of LSC.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. An apparatus for viewing a surface comprising:
    an examining instrument, the examining instrument having an imaging path through which the surface is observed;
    a Xenon light source, the light source illuminating the surface;
    an imager, the imager detecting light reflected from the surface, and generating image signals;
    a camera control unit (CCU), the CCU processing the image signals; and
    a controller associated with the imager and CCU, the controller having software executing on the controller the controller including an exposure value $EV_i$, $EV_i$ being used to control the output intensity of the light source by decrementing or incrementing the intensity of the light source output via at least two steps,
    wherein the controller decrements or increments the intensity of the light source output via a plurality of steps,
    wherein the intensity of the at least two steps is incremented or decremented by a predetermined percentage of the maximum light source output intensity,
    wherein the controller increments or decrements the output intensity of the light source via a power scan method the power scan method being able to increment or decrement the output intensity of the light source with a specified step $\Delta P_{scan}$, from $P_{scan,min}$ to $P_{max}$, where $P_{scan,min}$ is less than $P_{max}$, and $P_{max}$ is the maximum allowed light source output intensity,
    wherein the power scan method is enabled by a scan request method, the scan request method being able to detect a potential safety issue,
    wherein the controller compensates for the disadvantages of high frequency noise and slow response of a Xenon or a Xenon-like light source output by using the scan request method that involves a correlation method allowing for decrementing the output intensity with a specified step $\Delta P_{scan}$.

2. The apparatus of claim 1, further comprising a communication bus coupled to a plurality of bus interfaces for communication between the light source and the CCU.

3. The apparatus of claim 1, wherein the light source has at least one of high-frequency noise, slow-response time, non-linearity, and non-monotonic response time.

4. The apparatus of claim 1, wherein the examining instrument is selected from a group consisting of an endoscope, laryngoscope, bronchoscope, fiberscope, duodenoscope, gastroscope, flexible endoscope, arthroscope, cystoscope, laparoscope, anoscope, and sigmoidoscope.

5. The apparatus of claim 1, wherein the controller processes the image signals representative of light reflected from the surface.

6. The apparatus of claim 1, wherein the imager is either located distally inside the examining instrument, proximately inside the examining instrument, or externally from the examining instrument.

7. The apparatus of claim 1, wherein the imager is a CCD or CMOS imager.

8. The apparatus of claim 1, further comprising software executing on the controller.

9. The apparatus of claim 8, wherein the controller includes an exposure value $EV_i$, $EV_i$ being used to control the output intensity of the light source.

10. The apparatus of claim 9, wherein measured $EV_i$ is $EV_{meas}$, and wherein when $EV_{meas}$ is below the threshold $EV_{tr}$, the light source output intensity is reduced.

11. The apparatus of claim 10, wherein the optimal value of $EV_i$, $EV_{opt}$, is between $EV_{opt,min}$ and $EV_{opt,max}$, wherein $EV_{opt}$ depends on $EV_{meas}$, the monotonic and linearity characteristics of the light source output.

12. The apparatus of claim 11, wherein if $EV_{meas}$ is less than $EV_{opt,min}$, the output intensity of the light source is decremented, wherein if $EV_{meas}$ is greater than $EV_{opt,max}$, the output intensity of the light source is incremented, and wherein if $EV_{meas}$ is between $EV_{opt,min}$ and $EV_{opt,max}$, the output intensity of the light source is unchanged.

13. The apparatus of claim 11, wherein $EV_{meas}$ is between $EV_{opt,min}$ and $EV_{opt,max}$.

14. The apparatus of claim 1, wherein the apparatus minimizes the number of increments or decrements of light output intensity.

15. The apparatus of claim 1, wherein the controller is not continuously enabled to minimize flickering of the images.

16. The apparatus of claim 1, wherein when scan request method detects a potential safety issue, the correlation method is enabled and the EV method is disabled, and wherein when the potential safety issue is not detected the correlation method is disabled and the EV method is enabled.

17. The apparatus of claim 16, wherein the increment of power and correlation method are enabled and/or disabled based on the detection of the potential safety issue.

18. The apparatus of claim 1, wherein the output intensity of the light source is automatically reduced to a safe level when the light source output is not directed at a surface.

19. The apparatus of claim 1, wherein the intensity of the light source is automatically reduced to a safe level when at least one of the camera head, image sensor and light source and/or light guide are disconnected.

20. The apparatus of claim 1, wherein the controller includes adaptive normalization and self-calibration.

21. The apparatus of claim 20, wherein adaptive normalization includes normalizing EV and recomputing calibration curves based on the type of light source and the type of image sensor.

22. The apparatus of claim 20, wherein the adaptive normalization and self-calibration depends on integration time $T_{int}$, $EV_{min}$ and $EV_{max}$.

23. The apparatus of claim 1, wherein the controller detects when no motion is present in the video images in order to decrease output intensity to a safe level.

24. The apparatus of claim 1, wherein the controller compensates for the slow response of Xenon light source by inserting optimal delays before and/or after controlling of the light source.

25. An apparatus for viewing a surface comprising:
    an examining instrument, the examining instrument having an imaging path through which the surface is observed;
    a Xenon light source, the light source illuminating the surface;
    an imager, the imager detecting light reflected from the surface, and generating image signals;
    a camera control unit (CCU), the CCU processing the image signals;
    a controller associated with the imager and CCU, the controller having software executing on the controller, the controller including an exposure value $EV_i$, $EV_i$ being used to control the output intensity of the light source by decrementing the intensity of the light source output via at least two steps, wherein the controller increments or decrements the output intensity of the light source via a power scan method the power scan method being able to increment or decrement the output intensity of the light source with a specified step $\Delta P_{scan}$, from $P_{scan,min}$ to $P_{max}$, where $P_{scan,min}$ is less than $P_{max}$, and $P_{max}$ is the maximum allowed light source output intensity, wherein the power scan method is enabled by a scan request method, the scan request method being able to detect a potential safety issue, wherein the controller compensates for the disadvantages of high frequency noise and slow response of a Xenon or a Xenon-like light source output by using the scan request method that involves a correlation method allowing for decrementing the output intensity with a specified step $\Delta P_{scan}$.

26. The apparatus of claim 25, wherein the light source has at least one of high-frequency noise, slow-response time, nonlinearity, and non-monotonic response time.

27. The apparatus of claim 25, wherein the examining instrument is selected from a group consisting of an endoscope, laryngoscope, bronchoscope, fiberscope, duodenoscope, gastroscope, flexible endoscope, arthroscope, cystoscope, laparoscope, anoscope, and sigmoidoscope.

28. A method for controlling the light output intensity of a Xenon light source comprising:
measuring an exposure value $EV_i$, $EV_i$ being used to control the output intensity of the Xenon light source; and
incrementing or decrementing the output intensity of the Xenon light source based upon the exposure value $EV_i$,
wherein the step of incrementing or decrementing the output intensity of the Xenon light source is done via a power scan method, the power scan method being able to increment or decrement the output intensity of the light source with a specified step $\Delta P_{scan}$, from $P_{scan,min}$ to $P_{max}$, where $P_{scan,min}$ is less than $P_{max}$, and $P_{max}$ is the maximum allowed light source output intensity,
wherein the power scan method is enabled by a scan request method, the scan request method being able to detect a potential safety issue,
wherein the scan request method involves a correlation method allowing for decrementing the output intensity with a specified step $\Delta P_{scan}$.

29. The method of claim 28, wherein measured $EV_i$ is $EV_{meas}$, and when $EV_{meas}$ is below the threshold $EV_{tr}$, the light source intensity is immediately reduced.

30. The method of claim 28, wherein the optimal value of $EV_i$, $EV_{opt}$, is between $EV_{opt,min}$ and $EV_{opt,max}$, wherein $EV_{opt}$ depends on $EV_{meas}$, and the monotonic and linearity characteristics of the light source.

31. The method of claim 28, wherein if $EV_i$, is less than $EV_{opt,min}$, the output intensity of the light source is decremented, wherein if $EV_i$ is greater than $EV_{opt,max}$, the output intensity of the light source is incremented, and wherein if $EV_i$ is between $EV_{opt,min}$ and $EV_{opt,max}$, the output intensity of the light source is unchanged.

32. The method of claim 28, wherein $EV_{meas}$ is between $EV_{opt,min}$ and $EV_{opt,max}$.

33. An apparatus for viewing a surface comprising:
an examining instrument, the examining instrument having an imaging path through which the surface is observed;
a light source, the light source illuminating the surface;
an imager, the imager detecting light reflected from the surface, and generating image signals;
a camera control unit (CCU), the CCU processing the image signals; and
a controller associated with the imager and CCU, the controller including an exposure value $EV_i$, $EV_i$ being used to control the output intensity of the light source by decrementing the intensity of the light source output via incremental steps, the incremental steps being a predetermined percentage of the maximum light source output intensity,
wherein the light source has at least one of high-frequency noise, slow-response time, nonlinearity, and non-monotonic response time,
wherein the controller increments or decrements the output intensity of the light source via a power scan method the power scan method being able to increment or decrement the output intensity of the light source with a specified step $\Delta P_{scan}$, from $P_{scan,min}$ to $P_{max}$, where $P_{scan,min}$ is less than $P_{max}$, and $P_{max}$ is the maximum allowed light source output intensity,
wherein the power scan method is enabled by a scan request method, the scan request method being able to detect a potential safety issue,
wherein the controller compensates for the disadvantages of high frequency noise and slow response of a Xenon or a Xenon-like light source output by using the scan request method that involves a correlation method allowing for decrementing the output intensity with a specified step $\Delta P_{scan}$.

34. An apparatus for viewing a surface comprising:
an examining instrument, the examining instrument having an imaging path through which the surface is observed;
a light source, the light source illuminating the surface;
a CMOS imager, the CMOS imager detecting light reflected from the surface, and generating image signals;
a camera control unit (CCU), the CCU processing the image signals; and
a controller associated with the CMOS imager and CCU, the controller including an exposure value $EV_i$, $EV_i$ being used to control the output intensity of the light source by decrementing the intensity of the light source output via incremental steps,
wherein the controller increments or decrements the output intensity of the light source via a power scan method the power scan method being able to increment or decrement the output intensity of the light source with a specified step $\Delta P_{scan}$, from $P_{scan,min}$ to $P_{max}$, where $P_{scan,min}$ is less than $P_{max}$, and $P_{max}$ is the maximum allowed light source output intensity,
wherein the power scan method is enabled by a scan request method, the scan request method being able to detect a potential safety issue,
wherein the controller compensates for the disadvantages of high frequency noise and slow response of a Xenon or a Xenon-like light source output by using the scan request method that involves a correlation method allowing for decrementing the output intensity with a specified step $\Delta P_{scan}$,
wherein the light source has at least one of high-frequency noise, slow-response time, nonlinearity, and non-monotonic response time.

35. A method for protection from a high intensity output of a light source having at least one of high-frequency noise, slow-response time, nonlinearity, and non-monotonic response time, the method comprising the steps of:
measuring an exposure value $EV_{meas}$, $EV_{meas}$ being used to control the output intensity of the light source; and
incrementing or decrementing the output intensity of the light source $P_{scan}$ based upon the exposure value $EV_{meas}$ via a power scan method, the power scan method being able to increment or decrement the output intensity of the light source with a specified step $\Delta P_{scan}$, from $P_{scan,min}$ to $P_{max}$, where $P_{scan,min}$ is less than $P_{max}$, and $P_{max}$ is the maximum allowed light source output intensity, wherein the power scan method is enabled by a scan request method, the scan request method being able to detect a potential safety issue, wherein the scan request method involves a correlation method allowing for decrementing the output intensity with a specified step $\Delta P_{scan}$;

determining an optimal value of $EV_{meas}$, which is $EV_{opt}$, $EV_{opt}$ being between $EV_{opt,min}$ and $EV_{opt,max}$, and $EV_{opt}$ being dependent on the monotonic and linearity characteristics of the light source, wherein if $EV_{meas}$ is less than $EV_{opt,min}$, the output intensity is decremented, wherein if $EV_{meas}$ is greater than $EV_{opt,max}$, the output intensity is incremented, and wherein if $EV_{meas}$ is between $EV_{opt,min}$ and $EV_{opt,max}$, the output intensity is unchanged.

36. An apparatus for protection from a high intensity endoscopic light source output comprising:

an endoscope having an imaging path through which a surface at a distal end can be observed;

a Xenon light source for illumination of the surface;

an imager detecting light reflected from the surface and generating image signals;

a camera control unit (CCU) processing the image signals received from the imager, the camera control unit including a controller, the controller including an exposure value $EV_i$, $EV_i$ being used to control the output intensity of the light source, the controller being able to increment or decrement the output intensity of the Xenon light source, the controller being able to decrement or increment the intensity of the light source output via a plurality of steps, the intensity of the at least two steps is incremented or decremented by a predetermined percentage of the maximum light source output intensity, such that if the controller detects a potential safety issue, the Xenon light source output intensity $P_{scan}$ is adjusted via at least one discrete step $\Delta P_{scan}$, from $P_{min}$ to $P_{max}$; where $P_{scan}$ is less than $P_{max}$, and $P_{max}$ is the maximum allowed light source output intensity; and a communication bus coupled to a plurality of bus interfaces for communication between the Xenon light source and the camera control unit.

37. The apparatus of claim 20, wherein the adaptive normalization and self-calibration includes a self-recovery method.

38. The method of claim 37, further comprising a self-recovery step that re-computes at least one of processing coefficients, equations, and/or calibration curves used to compute $EV_{opt}$.

39. The apparatus of claim 1, wherein the intensity of the at least two steps is incremented or decremented in intervals as small as 1% of the total light source intensity.

* * * * *